United States Patent [19]

Brot et al.

[11] Patent Number: 4,661,443

[45] Date of Patent: Apr. 28, 1987

[54] ASSAY FOR MEASURING GENE EXPRESSION

[75] Inventors: Nathan Brot, West Orange; Herbert Weissbach, Cedar Grove, both of N.J.

[73] Assignee: Hoffmann-La Roche Inc., Nutley, N.J.

[21] Appl. No.: 712,283

[22] Filed: Mar. 15, 1985

Related U.S. Application Data

[63] Continuation of Ser. No. 405,667, Aug. 6, 1982, abandoned.

[51] Int. Cl.$^4$ .......................... C12Q 1/68; C12P 21/00; C12P 21/02; C12P 19/34; G01N 33/48; G01N 33/00

[52] U.S. Cl. .......................................... 435/6; 435/68; 435/70; 435/91; 436/63; 436/94; 935/44; 935/79

[58] Field of Search .................. 435/68, 70, 6, 91, 317, 435/172.3; 436/94, 63; 935/44, 79

[56] References Cited

PUBLICATIONS

Cenatiempo et al: "Use of Different tRNA$^{Ser}$ Isoacceptor Species in Vitro to Discriminate Between the Expression of Plasmid Genes", Proc. Natl. Acad. Sci. USA 79: 1466 (1982).

Robakis et al, "Translational Control of Ribosomal Protein L10 Synthesis Occurs Prior to Formation of First Peptide Bond", Proc. Natl. Acad. Sci. USA 78: 4261 (1981).

Goldberg et al, "In Vitro Regulation of DNA–Dependent Synthesis of *Escherichi coli* Ribosomal Protein L12", Proc. Natl. Acad. Sci. USA 76: 1716 (1979).

Modolell, "The Initial Steps in Protein Synthesis: Effects by Antibiotics", Methods in Enzymology, vol. 30, Part F, pp. 79–86 (1974).

*Primary Examiner*—James Martinell
*Attorney, Agent, or Firm*—Jon S. Saxe; George M. Gould; Norman C. Dulak

[57] ABSTRACT

A DNA-directed in vitro assay for measuring the formation of the initial NH$_2$-terminal dipeptides or tripeptides which are characteristic of a particular gene product is disclosed. This invention also encompasses a kit consisting of the reagents necessary to perform this method so as to measure or identify a product of gene expression.

27 Claims, 7 Drawing Figures

4,661,443

ASSAY FOR MEASURING GENE EXPRESSION

This is a continuation of application Ser. No. 405,667, filed Aug. 6, 1982, now abandoned.

FIELD OF THE INVENTION

This invention relates to improved methods and kits for measuring the product of gene expression.

BACKGROUND ART

Several DNA-directed in vitro protein synthesizing systems have been developed to study the regulation of gene expression.[1,2] Most laboratories use a modification of the original unfractionated system described by Zubay and coworkers,[3] but a highly defined system has also been described.[4,5] In most cases, the synthesized complete protein product is assayed by using gel electrophoresis and/or immunoprecipitation techniques; procedures that are long and rather complicated and often involve numerous reagents. In some instances, enzymatic assay of the product is possible, e.g. β-galactosidase,[3] but this depends on the gene product and the activity of the in vitro synthesizing system.

SUMMARY OF THE INVENTION

Figure 1:
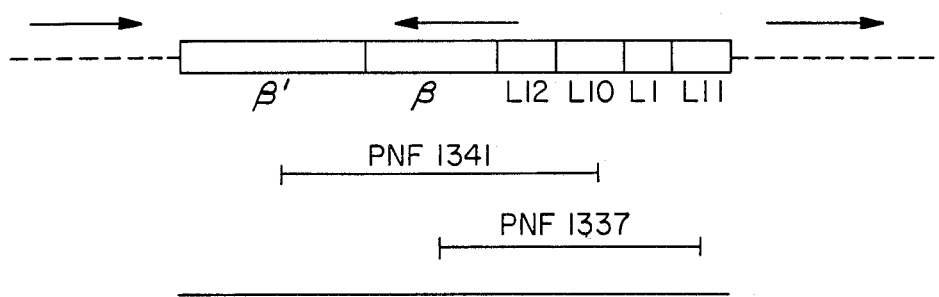
FIG. 1: Map of the bacterial inserts on plasmids pNF1337 and pNF1341.

This invention comprises a DNA-directed in vitro method which measures the formation of the initial dipeptide or tripeptide characteristic of the gene product. It is preferrably used with templates which contain a limited number of genes, such as plasmids, DNA restriction fragments, and where the N-terminal sequence of the protein product is known. Measuring a dipeptide provides specificity, is quantitative and the product can be easily and quickly assayed. The system can be constructed with 5 highly purified factors (defined system) or with a ribosomal high salt wash (RSW[6]) fraction plus RNA polymerase (crude system).

Dipeptide and tripeptide synthesis can be specifically obtained by limiting the acylated tRNA species that are used in the system. Thus, by using fMet-tRNA and the appropriate aminoacyl-tRNA species for the second and third amino acid, a specific di- or tripeptide gene product can be selectively synthesized. Additionally, measurement of a tripeptide can be used as a rapid, specific and quantitative assay of the amount of a particular mRNA template present in a mixture of mRNA species. Since di- or tripeptide formation from a DA template involves accurate transcription and proper initiation oof translation, this system is useful for studies on the regulation of gene expression.

DETAILED DESCRIPTION OF THE INVENTION

Broadly stated, in one preferred embodiment this invention comprises an in vitro assay for determining whether the initial dipeptides, characteristic of a specific gene expression product, have been formed, which assay comprises:

a. reacting a DNA template in an in vitro incubation mixture with a labeled or unlabeled methionine t-RNA, said methioninyl t-RNA being incorporated as the first amino acid of the in vitro formed dipeptide;

b. concurrently with step a, reacting the DNA template in said in vitro incubation mixture with a second labeled or unlabeled t-RNA, said second t-RNA corresponding to the second amino acid present in the specific dipeptide of said specific gene expression product;

c. incubating the reaction mixture of steps a and b for a period of time and at a temperature adequate for the reactions to be substantially completed;

d. adding a quantity of base to the mixture of step c sufficient to halt the reactions and hydrolyze the dipeptide from the t-RNA;

e. separating the dipeptides formed by the reactions from the reaction mixture of step d; and f. measuring the dipeptides separated in step e for the presence of labeled peptides, whereby the presence of labeled peptides is indicative of the formation of the dipeptides characteristic of the specific gene expression product, provided, however, that at least one of said t-RNAs of steps a and b are labeled.

This invention also comprises another preferred embodiment an in vitro assay for determining whether the initial tri-peptide, characteristic of a specific gene expression product, have been formed, which assay comprises:

a. reacting a DNA template in an in vitro incubation mixture with labeled or unlabeled methionine, said methionine t-RNA being incorporated as the first amino acid of the in vitro formed tripeptide;

b. concurrently with step a, reacting the DNA template with a labeled or unlabeled second t-RNA, said second t-RNA corresponding to the second amino acid present in the specific tripeptide of said specific gene expression product;

c. concurrently with steps a and b, reacting the DNA template with a third labeled or unlabeled t-RNA, said third labeled t-RNA corresponding to the third amino acid present in the specific tripeptide of said specific gene expression product;

d. incubating the reaction mixture of steps a, b and c for a period of time and at a temperature adequate for the reactions to be substantially completed;

e. adding a quantity of base to the mixture of step d sufficient to halt the reactions and hydroolyze the tripeptide from the t-RNA;

f. separating the tripeptides formed by the reactions from the mixture of step e; and g. measuring the tripeptides separated in step f for the presence of labeled peptides whereby the presence of labeled peptides is indicative of the formation of the tripeptides characteristic of the specific gene expression product, h. measuring the tri-peptides separated in step g for the presence of labeled peptides whereby the presence of labeled peptides is indicative of the formation of the tripeptides characteristic of the specific gene expression product.

This invention additionally comprises a kit for the practice of the dipeptide assay which kit consists of:
a. an incubation mixture consisting essentially of initiation factors, elongation factor Tu, ribosomes, buffers, salts, nucleotide triphosphates and RNA polymerase, and
b. individual bottles each containing labeled or unlabeled methionine t-TNA and other selected labeled or unlabeled t-RNA reagents.

The kit of this invention additionally contains a means for separating the reaction product formed by the di-peptide or tri-peptide assays from the reaction mixture and a means for measuring the reaction product for labeled di- or tri-peptides. As used herein, the term "labeled tRNA" represents a labeled amino acid attached to a tRNA. The labeling preferred for use herein is radioactive labeling although any procedure known to those skilled in the art for measuring the di- and tri-peptides may be used. Additionally, this invention can also be used with an mRNA template as opposed to a DNA template.

Restriction endonuclease Hinc II was purchased from Bethesda Research Laboratories, Inc. (Gaithersburg, MD) and Hind III from New England Biolabs (Beverly, MA). Unfractionated E. coli tRNA, purified tRNA$_f^{Met}$, phosphoenolpyruvate (PEP) and pyruvate kinase (PK) were purchased from Boehringer-Mannheim. Purified tRNA isoacceptor species tRNA$_1^{Ser}$, tRNA$_3^{Ser}$, tRNA$_3^{Ala}$, and tRNA$_4^{Leu}$ were kindly supplied by Dr. B. R. Reid, University of Washington, Seattle. A 0.25M salt eluate from a DEAE-cellulose column was used as the source of the enzymes required to acylate and transformylate the tRNA species.[7] The acylation and transformylation reactions were carried out as described elsewhere.[8-11] The acylated tRNA species were purified as previously described.[12] An E. coli RSW was prepared by washing ribosomes with 1.0M NH$_4$Cl as described previously.[7] The extract was dialyzed against a buffer containing 10 mM Tris-acetate, pH 8.2, 14 mM Mg$^{2+}$ acetate; 60 mM K$^+$ acetate, and 1 mM DTT. High salt washed 70S ribosomes and initiation factors IF-1, IF-2 and IF-3 were prepared as described.[13,14] EF-Tu was prepared according to Miller and Weissbach[15] and EF-G according to Rohrbach et al.[16] RNA polymerase was prepared according to the method of Burgess.[17]

N-formyl-L-methionine, N-formyl-L-methionyl-L-alanine, L-methionyl-L-serine and spermidine were purchased from Sigma Chemical Co. L-methionyl-L-leucine was obtained from Vega Biochemicals. N-formyl-L-methionyl-L-alanyl-L-leucine was kindly supplied by Dr. W. Danho (Hoffmann-La Roche, Inc.). N-formyl-L-methionyl-L-serine and N-formyl-L-methionyl-L-leucine were prepared as described previously.[12] PEG 6000 was obtained from J. T. Baker Chemical Co., precoated thin layer chromatography plates (Silica Gel G, 250 μM) from Analtech (Newark, DE), and Seakem and Seaplaque agarose from FMC Corporation, Rockland, ME. L-[$^3$H]alanine, L-[$^3$H]serine, and L-[$^3$H]leucine were obtained from New England Nuclear, L-[$^{35}$S]methionine was from Amersham/Searle. All radioactive samples were dissolved in Brays Solution (National Diagnostics) and counted in a liquid scintillation spectrometer.

The following plasmids were used herein in the practice of this invention.

Escherichia coli JF943 containing either plasmid pNF1337 or pNF1341 was kindly supplied by Dr. J. Friesen (University of Toronto, Toronto, Canada). The plasmid DNA was isolated from this transformant and used to transform E. coli strain RRI.[18] Strain RRI was also used as host for plasmids pBR322[19] and pJEA4. Plasmid pJEA4 was prepared (from plasmid pSoe3101)[20] by Dr. J. Erion in this laboratory and has a 2.2 kbp fragment that contains the gene for the large subunit of spinach RUBPCase.[21]

Plasmid pNF1337 was used as a DNA template for most of the studies described here (FIG. 1). This plasmid has a bacterial insert (cloned into pBR322) that starts at condon 106 of ribosomal protein L11 and contains all of the genetic information for ribosomal proteins L1, L10, and L12, and terminates within the gene coding for the β subunit of RNA polymerase.[22] This gene cluster is inserted into pBR322 at the Pst I restriction endonuclease site and therefore plasmid pNF1337 contains a truncated β-lactamase gene.[22] Since it has been shown that ribosomal protein L1 cannot be synthesized from pNF1337 DNA,[23] the only bacterial genes expressed are L10, L12 and the NH$_2$-terminal fragment of the β subunit. DNA sequence studies of this genetic region[24] have revealed that the N-terminal nascent dipeptides of these proteins are fMet-Ala (L10), fMET-Ser (L12) and fMet-Val (β-subunit). Similar studies of the β-lactamase gene have shown that the N-terminal dipeptide of this enzyme is fMet-Ser.[25] Like pNF1337, pNF1341 also contains a fragment of λrif$^d$18 DNA but the insert begins at condon 26 of the L10 gene and extends through the L12 and the β subunit genes (FIG. 1).[22] This DNA, therefore, lacks both the promoter and NH$_2$-terminal fragment of L10.

DNA fragments and mRNA were prepared as follows.

Figure 2:
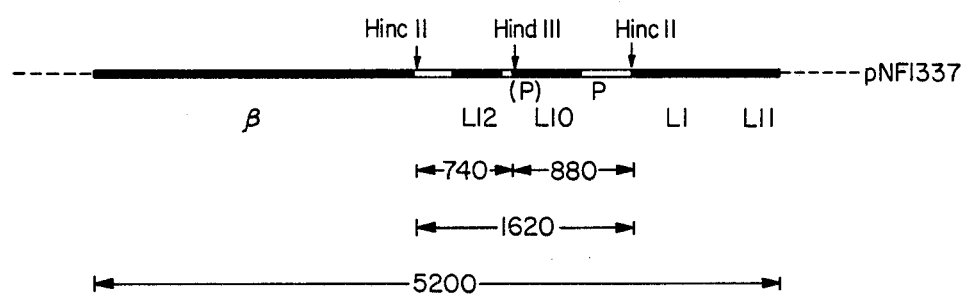
FIG. 2: Partial restriction map of the bacterial DNA inserted into plasmid pBR322.

A 1.6 kbp DNA fragment containing the entire genes for ribosomal proteins L10 and L12 was prepared by digestion of the plasmid pNF1337 with restriction endonuclease Hinc II. This fragment also contains the genetic information for several amino acids at the carboxyl terminus of ribosomal protein L1, and terminates within the leader sequence of the β subunit of RNA polymerase (FIG. 2). Further restriction digestion of the 1.6 kbp DNA fragment with Hind III yields two fragments. One of them is 880 bp long and contains the promoter region and coding sequences for approximately 90% of the L10 gene product. The smaller fragment (740 bp) contains the remainder of the L10 gene and the entire L12 gene (FIG. 2). The L12 gene should not be expressed to any significant extent from this fragment since the fragment is missing a functional promoter.[23,26,27] mRNA templates were synthesized from plasmid pNF1337, the Hinc II fragment and the Hind III restriction digest of the 1.6 kbp fragment.

The following procedure was used to obtain the 1.6 kbp Hinc II fragment and the 880 bp Hind III fragment. The reaction mixture contained: 10 mM Tris-HCl, pH 7.9, 1 mM dithiothreitol (DTT), 30 mM NaCl, 1 mM MgCl$_2$, 0.6 mg/ml of DNA, one enzyme unit (Hinc II) per μg DNA and 100 μg/ml of nuclease free BSA. The extent of digestion was determined by analytical agarose gel electrophoresis (1.2% Seakem). After digestion was complete, the reaction mixture was extracted with an equal volume of a phenol:chloroform mixture (1:1) saturated with electrophoresis buffer (40 mM Tris-acetate, pH 7.8, 5 mM Na$^+$ acetate, 1 mM EDTA). The aqueous phase was made 0.3M in Na$^+$ acetate and the DNA was precipitated with ethanol. The precipitate was dissolved in electrophoresis buffer, glycerol added (final concentration 25%) and the sample was electrophoresed overnight at 25 mA in a 1.2% Seakem agarose gel. After staining with ethidium bromide, the band containing the 1.6 kbp fragment was excised and the 1.6 kbp fragment was isolated by the procedure of Thuring et al.[28] In brief, the agarose band was cut into small pieces (approximately $1 \times 0.5 \times 0.5$ cm), frozen at $-20°$ C., and then placed individually into a petri dish between two parafilm sheets. The agarose was pressed by hand between the two parafilm sheets until fluid was expressed. The droplets were collected, extracted with buffer saturated phenol, and the DNA was precipitated with ethanol. The Hinc II 1.6 kbp DNA prepared in this way was incubated with Hind III in the following buffer: 7 mM Tris-HCl, pH 7.4; 60 mM NaCl; 7 mM $MgCl_2$; 100 µg/ml BSA; 0.2 mg/ml DNA and one Hind III unit per µg of DNA. The mixture was incubated at 37° C. for about one hr. After complete digestion, the mixture was kept at 4° C. and could be used for mRNA synthesis without further treatment.

Table I lists the genes present on plasmid pNF1337, the amino terminal peptides for each gene product, the codewords for each amino acid (from the DNA sequences) and the tRNA isoacceptor species that are required.

mRNA was prepared by incubating 40 µg of plasmid DNA or a restriction fragment at 37° C. in the following reaction mixture (final volume 0.5 ml): 50 mM Tris-acetate, pH 7.5, [$^3$H]UTP (5,000 cpm/nmole), CTP, GTP, ATP, 0.8 mM each; DTT 1 mM; PEP 25 mM; PK 14 µg/ml, RNA polymerase 60 µg/ml, magnesium acetate 10 mM; spermidine 1 mM. At the end of the incubation, the reaction mixture was made 0.01% in $NaDodSO_4$ and extracted with phenol saturated with 50 mM Tris-HCl, pH 7.5. The aqueous phase was extracted three times with an equal volume of ether, and then concentrated 5-fold (Speed-Vac, Savant Instruments). The nucleic acids were precipitated by cold ethanol in the presence of 0.3M sodium acetate and the precipitate was dissolved in a small volume of sterile water to which three volumes of 4M $Na^+$-acetate was added. The mixture was left overnight at 4° C. and then placed at $-20°$ C. for about 2 hrs. The precipitated mRNA was collected by centrifugation and redissolved in sterile water. The DNA fragment in the supernatant could be recovered by overnight dialysis against 5 mM Tris-HCl, pH 7.5, followed by concentration and ethanol precipitation as described above. The recovered DNA was active as a template in the dipeptide system (see below).

DNA-DIRECTED DIPEPTIDE SYNTHESIS (FMET-ALA)

The expression of the L10 gene, as measured by fMet-Ala formation (Table I) is used here as an example although the system as described could be used for other dipeptides directed by different templates.

TABLE I

| Plasmid | Different Plasmids Used and Peptide Products[a] | | | |
|---|---|---|---|---|
| | Gene product | $NH_2$—terminal sequence | Nucleotide coding sequence | Second codon isoacceptor tRNA |
| pNF1337 | Ribosomal protein L10 | fMet—Ala | AUG GCU | $Ala_{3 \text{ or } 2}$ |
| pNF1337 | Ribosomal protein L12 | fMet—Ser | AUG UCU | $Ser_{1 \text{ or } 2}$ |
| pNF1337 | β Subunit | fMet—Val | AUG GUU | $Val_1$ |
| pNF1337 PBR322 | β-Lactamase | fMet—Ser | AUG AGU | $Ser_3$ |

[a]Adapted, in part, from Y. Cenatiempo, N. Robakis, L. Meza-Basso, N. Brot, H. Weissbach and B. R. Reid, Proc. Natl. Acad. Sci. USA 79, 1466 (1982).

Figure 3:
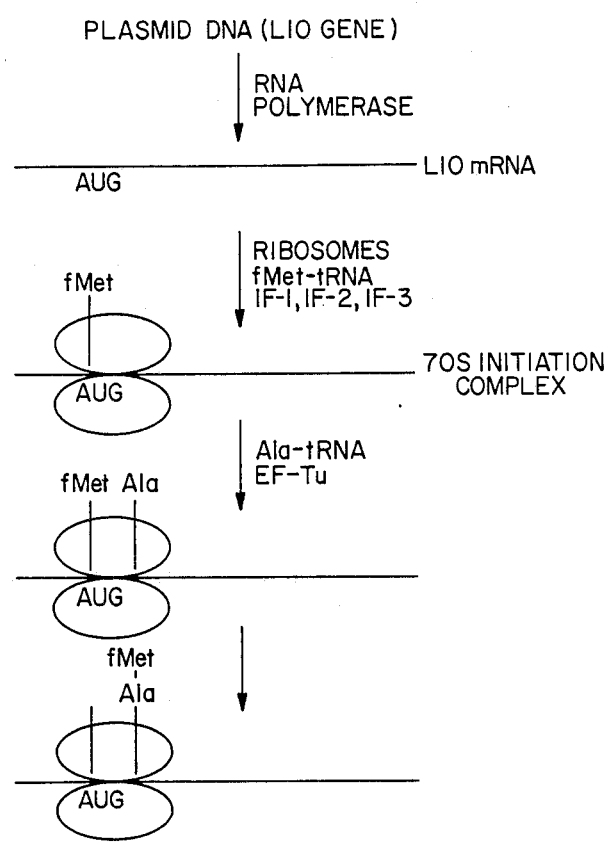
FIG. 3: Outline of steps leadiing to dipeptide formation in the in vitro system.

This was described in the publication by Robakis, et al. *Proc. Natl. Acad. Sci. USA*, Vol. 78, 4261 (1981) which is incorporated by reference herein. The steps involved in fMet-Ala formation starting with a DNA template are shown in FIG. 3. The in vitro incubation mixture, (final volume 35 µl) contains the following components: 30 mM Tris-acetate (pH 7.5); 10 mM sodium dimethylglutarate (pH 6.0); 36 mM ammonium acetate; 2 mM DTT; 9.2 mM magnesium acetate[29]; 2.9 mM ATP, 0.7 mM CTP, GTP and UTP; 28 mM PEP; 0.5 µg of PK; 39 mM $K^+$ acetate; 0.8 mM spermidine, 3 µl of 50% PEG 6000[30]; 0.3 µg IF-1, 0.5 µg IF-2, 0.6 µg IF-3, 1.0 µg EF-Tu, 2 µg of RNA polymerase, 0.5–1.0 $A_{260}$ of $NH_4Cl$-washed 70S ribosomes; 10 pmoles of either unlabeled fMet-tRNA$_f^{Met}$ or f[$^{35}$S]Met-tRNA$_f^{Met}$ (about 7,000 cpm/pmole) and 10 pmoles of [$^3$H]Ala-tRNA (about 6,000 cpm/pmole) prepared by acylating unfractionated *E. coli* tRNA with [$^3$H]alanine. The reaction is initiated by the addition of 2 µg of plasmid pNF1337 or 0.4 µg of a DNA fragment (see above). When mRNA (0.5 µg) is used as a template, RNA polymerase is omitted for the reaction mixture. The reaction mixture (in 1.5 ml Eppendorf tubes) is incubated at 37° C. for one hr. The reaction is stopped by the addition of 2.7 µl of 1N NaOH and the mixture is incubated for an additional 10 min at 37° C. to hydrolyze any peptidyl-tRNA. Two assays have been used to measure dipeptide formation. One is based on thin layer chromatography which gives chromatographic identification of the product. The other involves a simple extraction which is rapid and suitable for routine analysis once the dipeptide has been identified by thin layer chromatography.

The first assay is by thin layer chromatograhy to the alkalinized reaction mixture prepared as described above, 2 µl of a 10 mg/ml solution of fMet-Ala are added as carrier. The reaction misture is acidified by the addition of 4 µl of 2N HCl. The tubes are centrifued for 2 min. in an Eppendorf centrifuge 5414 and the precipitate is discarded. A portion of the supernatant (usually 24 µl) is applied in 3 µl aliquots to a silica gel G thin layer plate. The solvent system used is a mixture of ethyl acetate/hexanes/acetic acid, 8:3:1 (vol/vol). The plate is developed for 50 min. and after drying the methionine containing areas are visualized by exposing the plate to iodine vapor in a closed glass tank which contains iodine crystals. The fMet-Ala spot on the silica plate is scraped off into scintillation vials. The silica scaping is extracted with 1 ml of water for about 3 min. Nine ml of scintillation fluid are added and the radioactivity determined.

In this solvent system, fMet, fMet-Ala, and fMet-Ser display Rf values of 0.48, 0.37, and 0.2, respectively whereas all free amino acids remain at, or close to, the origin. Therefore, the system has also been used to study the synthesis of fMet-Ser (β-lactamase and L12). Usually for thin layer analysis, both the fMet-tRNA and second aminoacyl-tRNA are labeled but, if the dipeptide does not separate from free fMet (e.g. fMet-Val), only the second aminoacyl-tRNA should be labeled.

The second assay is performed by ethyl acetate extraction. This method is based on the extraction of the dipeptide from acidic solution into ethyl acetate. It is simpler and faster than the thin layer method described above. For these incubations, since fMet extracts into ethyl acetate under the conditions used, unlabeled fMet-tRNA is used and only the Ala-tRNA (or other second amino acid) is labeled. The reaction mixture after NaOH treatment (see above) is transferred to a glass test tube and 0.5 ml of 0.5N HCl is added followed by 3 ml of ethyl acetate. The tubes are mixed for a few sec (Vortex) and then centrifuged at low speed in a bench top centrifuge for 30 sec. Two ml of the ethyl acetate phase are transferred to a scintillation vial and the radioactivity measured. To determine the amount of product formed, the extractio coefficient of the different peptides must be known. Under the conditions used, about 75% of fMet-Ala and 30% of fMet-Ser extract into ethyl acetate.

Figure 4:
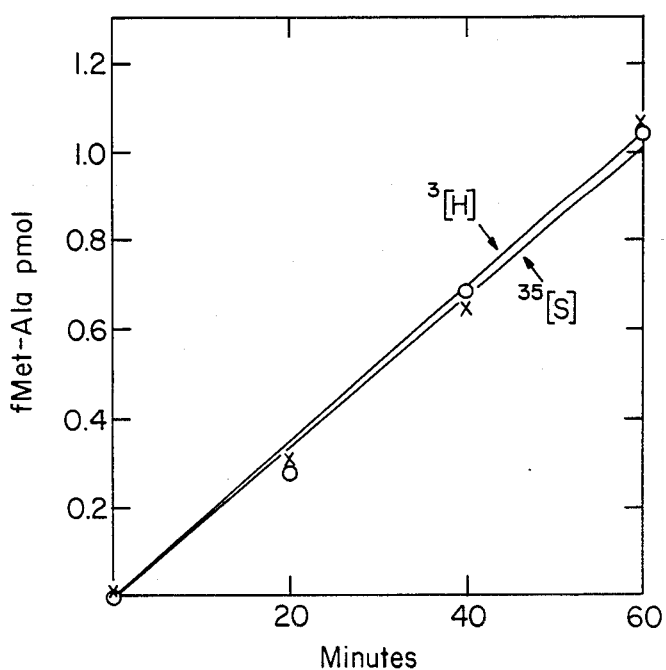
FIG. 4: Kinetics of fMet-Ala synthesis in the defined system.

FIG. 4 shows the kinetics of fMet-Ala synthesis in a defined system using plasmid pNF1337 as template. The synthesis of fMet-Ala is linear for at least 45-60 min when plasmid DNA or DNA fragments are used as templates. Similar results were obtained when other dipeptides were synthesized, e.g. fMet-Ser, fMet-Val. Table II shows the dependencies for the formation of fMet-Ala (or other dipeptides) in this system. With the exception of IF-1 there is an absolute requirement for all of the factors. Further evidence that fMet-Ala synthesis is due to the expression of the L10 gene is demonstrated by the absence of any fMet-Ala formation when plasmid pNF1341 (see FIG. 1) or pBR322 is used as a template instead of pNF1337.

TABLE II

Components Required for the Synthesis of fMet—Ala[a]

| Omission | fMet—Ala pmol |
| --- | --- |
| None | 1.7 |
| RNA polymerase | 0 |
| Ribosomes | 0 |
| IF-1 | 0.7 |
| IF-2 | 0 |
| IF-3 | 0 |
| EF-Tu | 0 |
| −1337 DNA + 1341 or pBR322 DNA | 0 |

[a]Details of the incubations are described in the text. Taken from N. Robakis, L. MezaBasso, N. Brot and H. Weissbach, Proc. Natl. Acad. Sci. USA 78, 4261 (1981), incorporated by reference herein.

The present system can efficiently use small DNA fragments and mRNA instead of plasmid DNA as templates. DNA fragments and mRNA were prepared as described above. The results are shown in Table III.

TABLE III fMet—Ala Synthesis Directed by DNA Fragments or mRNA[a]

| Template | fMet—Ala pmol |
| --- | --- |
| Hinc II DNA fragments | 3.0 |
| Hind III DNA fragments | 2.0 |
| mRNA prepared from Hinc II DNA fragments | 1.7 |
| mRNA prepared from Hind III DNA fragments | 1.5 |

[a]The details of the incubations and the preparation of the DNA fragments and mRNA are described in the text.

The dipeptide assay is not product specific if there are two genes on the template whose protein products begin with the same N-terminal dipeptide. To deal with this problem the dipeptide system can be moodified in two ways: (1) use of specific tRNA isoacceptor species, and (2) tripeptide formation.

1. Use of isoacceptor tRNA species

Unfractionated tRNA, acylated with a specific amino acid or purified tRNA isoacceptor species functions well in the system. If the codons for the second amino acid differ so that a different tRNA isoacceptor species is required for each gene product the dipeptides can be distinguished. An example of how condon specificity has been used to differentiate between the expression of the β-lactamase and L12 genes is shown here. As seen in Table I, both gene products begin with fMet-Ser but β-lactamase requires tRNA$_3^{Ser}$ whereas L12 uses tRNA$_1^{Ser}$. The reaction mixtures are essentially as described above for fMet-Ala synthesis, except that instead of [$^3$H]Ala-tRNA, 10 pmol of the purified isoacceptor [$^3$H]Ser-tRNA$_1^{Ser}$ or [$^3$H]Ser-tRNA$_3^{Ser}$ species are added. The results are shown in Table IV.

TABLE IV

Utilization of Two tRNA$^{Ser}$ Isoaccepting Species in the Dipeptide Assay[a]

| Template | Protein products containing fMet—Ser | Synthesis of fMet—Ser | |
| --- | --- | --- | --- |
| | | tRNA$_1^{Ser}$ | tRNA$_3^{Ser}$ |
| | | pmol | |
| pBR322 | β-lactamase | 0 | 4.0 |
| pNF1337 | L12, β-lactamase | 2.4 | 1.6 |
| Hinc II fragment | L12 | 1.2 | 0 |

[a]The reactions were carried out as described in the text, using 2 μg of plasmid DNA (pBR322, pNF1337) or 0.2 μg of the 1.6 kbp Hinc II DNA fragment (see Materials and Methods). Adapted, in part, from Y. Cenatiempo, N. Robakis, L. MezaBasso, N. Brot, H. Weissbach and B.R. Reid, Proc. Natl. Acad. Sci. USA 79, 1466 (1982).

With pBR322 as template, only tRNA$_3^{Ser}$ is active since β-lactamase is the primary gene product formed. Usig pNF1337 both tRNA$_3^{Ser}$ and tRNA$_1^{Ser}$ are active since both β-lactamase and L12 are formed. With the Hinc II DNA fragment, which directs the synthesis of L12, only tRNA$_1^{Ser}$ is active. Similar results have been obtained with plasmid pJEA4 which contains the gene for the large subunit of ribulose bisphosphate carboxylase oxygenase and the gene for β-lactamase. Both begin with fMet-Ser but the fMet-Ser synthesis from the large subunit gene uses tRNA$_1^{Ser}$, whereas β-lactamase synthesis requires tRNA$_3^{Ser21}$.

2. Synthesis of tripeptides

For tripeptide synthesis, e.g. fMet-Ala-Leu the N-terminal tripeptide of L10, the following modifications of the dipeptide system are made. Polyethylene glycol is omitted and 0.1 μg of EF-G, 10 pmol of [$^3$H]Leu-tRNA$_4^{Leu}$ (codon UUA) and non-radioactive Ala-tRNA$_3^{Ala}$ are added to the standard incubations for dipeptide synthesis. At the end of the incubation 20 μg of unlabeled fMet-Ala-Leu in 2 μl of H$_2$O are added, and the reaction mixture is treated as described above for dipeptide synthesis. The tripeptide can be separated by thin layer chromatography using the same solvent system described for fMet-Ala isolation (Rf 0.29). The tripeptide region is scraped from the plate and radioactivity determined as described above. The ethyl acetate extraction procedure can also be used. At 37°, tripeptide synthesis is linear for about 40 min but less tripeptide is formed than dipeptide. This lower tripeptide synthesis is not due to accumulation of the dipeptide, fMet-Ala, since under the conditions in which the tripeptide is made, there is no synthesis of dipeptide (Table V).

TABLE V

Comparison of Di- and Tripeptide Synthesis[a]

| | fMet—Ala | fMet—Ala—Leu |
|---|---|---|
| | | pmol |
| Dipeptide system | 2.0 | 0 |
| Tripeptide system | 0 | 0.6 |

[a]Plasmid 1337 was used as template. Di- and tripeptides were detected and separated by thin layer chromatography. The tripeptide system contained the components required for dipeptide synthesis plus EF-G and Leu-tRNA$_4^{Leu}$ except that polyethylene glycol 6000 was omitted from the reaction mixtures. Taken from Y. Cenatiempo, N. Robakis, B. R. Reid, H. Weissbach and N. Brot, in preparation.

Other experiments showed the fMet-Ala-Leu synthesis required all three acylated tRNA species and was markedly stimulated by EF-G.

Contrary to dipeptide synthesis, under the conditions used, tripeptide synthesis results in a stable tripeptidyl-tRNA.mRNA.ribosome complex and hence there is no recycling of the mRNA.[31] The higher level of dipeptide formation (Table V) is due to an instability of the dipeptidyl-tRNA.mRNA.ribosome complex and results in a recycling of the mRNA when only dipeptide synthesis occurs. Since tripeptides remain attached to 70S ribosomes, nitrocellulose filtration can also be used as an assay for the amount of tripeptide formed. In this case, at the end of the incubation, the reaction mixture is diluted to 0.3 ml with cold buffer containing 50 mM Tris-HCl pH 7.8, 100 mM NH$_4$Cl, 12 mM MgCl$_2$, and 2 mM $\beta$-mercaptoethanol and then rapidly passed through a nitrocellulose filter (0.45 $\mu$M, Millipore). The filter is washed three times with 3 ml of the same buffer and dissolved in scintillation fluid and the radioactivity determined. A comparison of di- and tripeptide formation using 2 different assays is shown in Table VI.

TABLE VI

Dipeptide and Tripeptide Synthesis by Different Assays[a]

| Assay | fMet—Ala | fMet—Ala—Leu |
|---|---|---|
| | pmol | |
| Thin layer | 2.5 | 0.9 |
| Filter | <0.1 | 0.8 |

[a]The assay systems and incubation conditions are described in the text except that polyethylene glycol 6000 was omitted from the reaction mixtures. Adapted, in part, from Y. Cenatiempo, N. Robakis, B. R. Reid, H. Weissbach and N. Brot, in preparation.

Although there is excellent dipeptide synthesis by the thin layer (or extraction) procedure, no stable complex, that is retained on a filter, is seen. This is due to rapid dissociation of the dipeptide ribosome complex. In contrast, there is reasonable agreement between the thin layer procedure and the filter assay for tripeptide synthesis. The above results suggested that tripeptide synthesis could also be used as a rapid and quantitative assay for the amount of a specific functional mRNA present in a mixture of mRNA species, since only those mRNA molecules that can bind to ribosomes and direct the synthesis of a specific tripeptide (active mRNA) would be measured.

Figure 5:
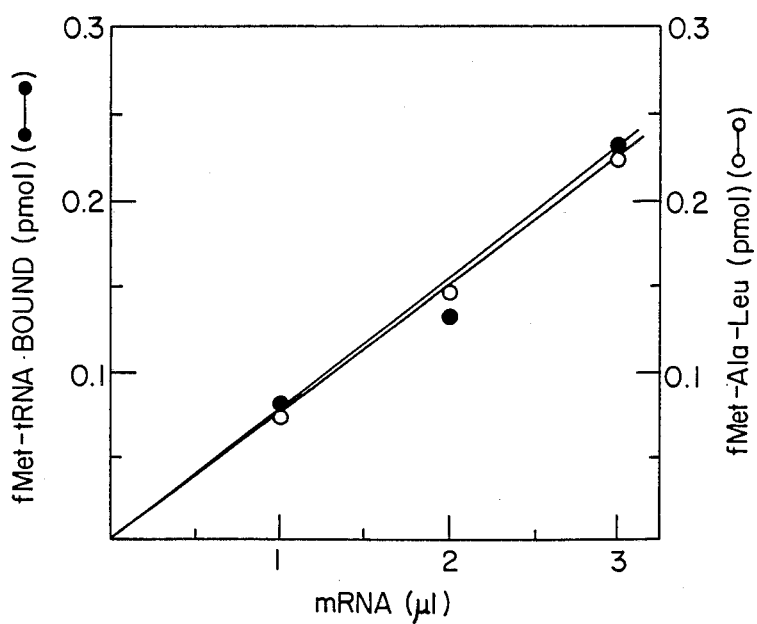
FIG. 5: fMet-tRNA binding to 70S ribosomes and tripeptide formation in the presence of various amounts of L10 mRNA.

To validate this procedure, the Hind III mRNA transcript containing the L10 mRNA was used. This mRNA preparation directs the synthesis of fMet-Ala but not fMet-Ser. It has onlyone fMet-tRNA binding site and fMet-tRNA binding should be a measure of the amount of mRNA present. FIG. 5 shows the results of a typical experiment comparing fMet-tRNA binding and tripeptide formation. An excellent correlation is obtained between the amount of fMet-tRNA bound and the amount of the tripeptide synthesized with limiting amounts of mRNA. A ribosomal high salt wash (RSW) may also preferably be used for di- and tripeptide synthesis.

Figure 6:
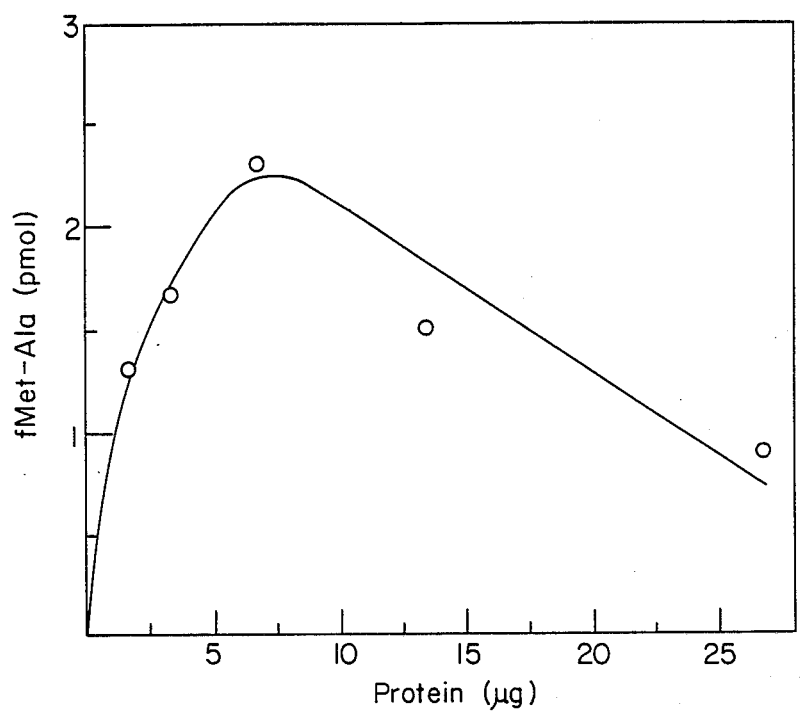
FIG. 6: Effect of ribosomal salt wash (RSW) protein on fMet-Ala formation.

The di- and tripeptide system as described above has the advantage that it is highly defined, but maynot be of general use since at least five purified factors are needed. Because of this, the system has been simplified by using a RSW instead of the purified initiation and elongation factors. For these experiments, the reaction mixture is similar to that described above, except that IF-1,IF-2,IF-3, EF-Tu and EF-G are omittedand replaced by a RSW preparation (6 $\mu$g protein). In addition to ribosomes, only RNA polymerase is required since it is not present in the RSW. The effect of RSW on fMet-Ala synthesis is seen in FIG. 6. It should be stressed that each RSW preparation must be titrated since inhibitory components are sometimes present in these extracts. As with the defined system, di- and tripeptides can be synthesized by this system and it can use plasmid DNA, DNA fragments or mRNA as templates. Both total E. coli tRNA or purified isoacceptor tRNA species can be used as a source of the acylated tRNAs.

Figure 7:
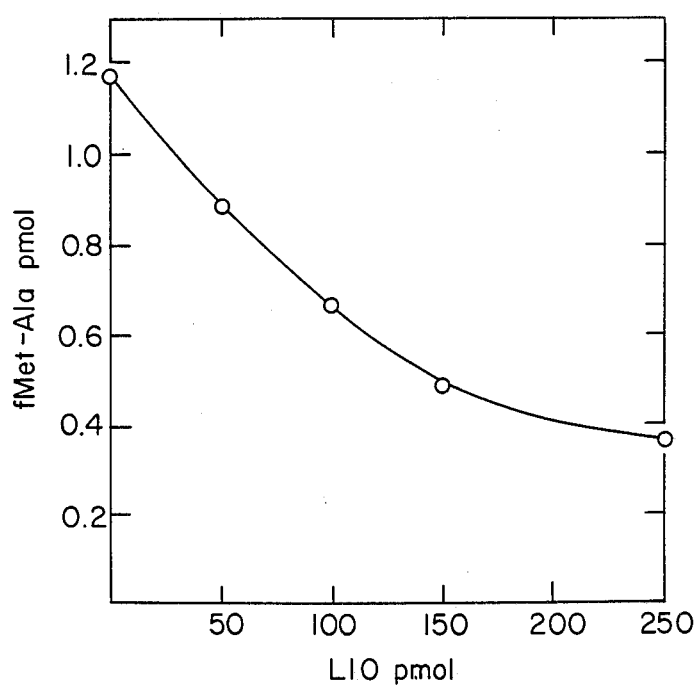
FIG. 7: Effect of protein L10 on fMet-Ala formation.

Di- or tripeptide synthesis can be used to study the regulation of gene expression at either the initiation of transcription or translation, and the system has been used to study the expression of both prokaryotic and chloroplast genes.[12,21] As an example, the effect of L10 on its own synthesis (autogenous regulation) has been investigated using the dipeptide system (fMet-Ala synthesis). Previous results had shown that the inhibition by L10 is at the level of translation but the site of inhibition has not been determined.[32] As shown in FIG. 7, L10 inhibits the synthesis of fMet-Ala indicating that the autoregulation occurs before the formation of the first peptide bond. This effect was shown to be specific since ribosomal protein L12 had no effect on the synthesis of fMet-Ala and L10 did not inhibit fMet-Ser formation (L12 or $\beta$-lactamase).[12] By examining the partial reactions involved in dipeptide formation (FIG. 3), it has been possible to show that L10 inhibits the formation of the 30S initiation complex.[33] Transcriptional control of fMet-Ala synthesis by guanosine-5'-diphosphate-3'-diphosphate has also been shown.[12]

REFERENCES

1. G. Zubay, Methods in Enzymology, Apr. 13, 1982.
2. B. de Crombrugghe, in: "Molecular Mechanism of Protein Biosynthesis" (H. Weissbach and S. Pestka, eds.), p. 603. Academic Press, Inc., New York, NY, 1977.
3. G. Zubay, D. A. Chambers and L. C. Cheong, in: ∂The Lactose Operon" (J. R. Beckwith and D. Zipser, eds.), p. 375. Cold Spring Harbor Laboratory, Cold Spring Harbor, NY, 1970.

4. H. F. Kung, B. Redfield, B. V. Treadwell, B. Eskin, C. Spears and H. Weissbach, *J. Biol. Chem.* 252, 6889 (1977).
5. T. Zarucki-Schulz, C. Jerez, G. Goldberg, H. F. Kung, K. H. Huang, N. Brot and H. Weissbach, *Proc. Natl. Acad. Sci. USA* 76, 6115 (1979).
6. The following abbreviations were used: RSW, ribosomal high salt wash; PEP, phosphoenolpyruvic acid; DTT, 1,5-dithiothreitol; TLC, thin layer chromatography; RUBPCase, ribulose bisphosphate carboxylase; PEG, polyethylene glycol 6000; BSA, bovine serum albumin; SA, specific activity; PK, pyruvates kinase.
7. H. F. Kung, C. Spears and H. Weissbach, *J. Biol. Chem.* 250, 1556 (1975).
8. H. W. Dickerman, E. Steers, Jr., B. Redfield and H. Weissbach, *J. Biol. Chem.* 242, 1522 (1967).
9. a. Böck, *Arch. Mikrobiol.* 68, 165 (1969).
10. K. L. Roy and D. Soll, *J. Biol. Chem.* 245, 1394 (1970).
11. P. Schofield, *Biochemistry* 9, 1694 (1970).
12. N. Robakis, L. Meza-Basso, N. Brot and H. Weissbach, *Proc. Natl. Acad. Sci. USA* 78, 4261 (1981).
13. N. Brot, E. Yamasaki, B. Redfield and H. Weissbach, *Biochem. Biophys. Res. Commun.* 40, 698 (1970).
14. J. W. B. Hershey, J. Yanov, K. Johnston and J. L. Faukunding, *Arch. Biochem. Biophys.* 182, 626 (1977).
15. D. L. Miller and H. Weissbach, *Arch. Biochem. Biophys.* 141, 26 (1970).
16. M. S. Rohrbach, M. E. Dempsey and J. W. Bodley, *J. Biol. Chem.* 249, 5094 (1974).
17. R. R. Burgess, *J. Biol. Chem.* 244, 6160 (1969).
18. F. Bolivar and K. Backman, *This Series* 68, 245 (1979).
19. F. Bolivar, R. Rodriguez, P. J. Greene, M. C. Betlach, H. L. Heyneker, H. W. Boyer, J. Crosa and S. Falkow, *Gene* 2, 95 (1977).
20. J. L. Erion, J. Tarnowski, H. Weissbach and N. Brot, *Proc. Natl. Acad. Sci. USA* 78, 3459 (1981).
21. Y. Cenatiempo, N. Robakis, L. Meza-Basso, N. Brot, H. Weissbach and B. R. Reid, *Proc. Natl. Acad. Sci. USA* 79, 1466 (1982).
22. N. P. Fiil, D. Bendiak, J. Collins and J. D. Fresen, *Mol. Gen. Genet.* 173, 39 (1979).
23. g. Goldberg, T. Zarucki-Schulz, P. Caldwell, H. Weissbach and N. Brot, *Biochem. Biophys. Res. Commun.* 91, 1453 (1979).
24. L. E. Post, P. D. Strycharz, M. Nomura, H. Lewis and P. P. Dennis, *Proc. Natl. Acad. Sci. USA* 76, 1697 (1979).
25. J. G. Sutcliffe, *Proc. Natl. Acad. Sci. USA* 75, 3737 (1978).
26. M. Yamamoto and M. Nomura, *Proc. Natl. Acad. Sci. USA* 75, 3891 (1978).
27. T. Linn and J. Scaife, *Nature* 275, 33-37 (1978).
28. R. W. J. Thuring, J. P. M. Sanders and P. Borst, *Anal. Biochem.* 66, 213 (1975).
29. The $Mg^{2+}$ concentration for optimal dipeptide synthesis should be titrated when the incubation components are changed (e.g. different ribosomes, tRNA).
30. Addition of PEG 6000 to the incubation mixture usually increases the yield of dipeptides by two-fold. This is probably due to the protection of mRNA against nucleases.
31. Yves Cenatiempo, Nikolaos Robakis, Brian R. Reid, Herbert Weissbach and Nathan Brot, submitted for publication.
32. N. Brot, P. Caldwell and H. Weissbach, *Proc. Natl. Acad. Sci. USA* 77, 2592 (1980).
33. N. Robakis, Y. Cenatiempo, S. Peacock, N. Brot and H. Weissbach, in: "Regulation of the Translational Process", (B. Safer and M. Grunberg-Manago, eds.), Elsevier North-Holland (1982), in press.

We claim:

1. A method for detecting the synthesis of a specific gene product in an in vitro protein synthesizing system capable of carrying out transcription and translation comprising:
   (a) reacting
      (i) an in vitro protein synthesizing system capable of carrying out transcription and translation which may contain a DNA template coding for a specific gene product, which specific gene product has
         A. An amino-terminal methioninyl residue, and
         B. an adjacent, second amino acid residue which differs from the corresponding residues of all other gene products formed in the system, with
      (ii) a mixture containing
         A. methioninyl t-RNA, and
         B. a second t-RNA charged with an amino acyl group corresponding to the second amino acid residue of the specific gene product,
      one or both of which t-RNA amino acyl groups is labeled, to allow formation of dipeptides;
   (b) incubating the reaction mixture for a period of time and at a temperature which would allow any dipeptide formation to be substantially complete;
   (c) adding a quantity of base that would be sufficient to stop any reaction and to hydrolyze any dipeptides formed from the t-RNA;
   (d) separating any dipeptides formed from the reaction mixture of step (c); and
   (e) detecting any separated dipeptides,
thereby detecting the synthesis of the specific gene product in the in vitro protein synthesizing system.

2. The method according to claim 1 in which a radioactive label is used.

3. The method according to claim 1 in which the in vitro protein synthesizing system comprises initiation factors, elongation factor Tu, ribosomes, buffers, salts, nucleoside triphosphates and RNA polymerase.

4. The method according to claim 3 in which the in vitro protein synthesizing system comprises Tris(hydroxymethyl)aminomethane-acetate, sodium dimethylglutarate, ammonium acetate, DTT, magnesium acetate, ATO, CTP, UTP, PEP, PK, potassium acetate, spermidine, PEG, RNA polymerase and $NH_4Cl$-washed 70S ribosomes.

5. The method according to claim 1 in which any dipeptides formed are separated from the reaction mixture by thin layer chromatography or by ethyl acetate extraction.

6. The method according to claim 2 in which any separated dipeptides are detected by measuring the radioactivity of the radioactive label.

7. The method according to claim 1 in which the reaction mixture is incubated at about 37° C. for about 1 hour.

8. The method according to claim 1 in which the base is 1N NaOH.

9. The method according to claim 8 in which the base treatment is carried out at about 37° C. for about 10 minutes.

10. A method for detecting the synthesis of a specific gene product in an in vitro protein synthesizing system capable of carrying out transcription and translation, comprising:
   (a) reacting
      (i) an in vitro protein synthesizing system capable of carrying out transcription and translation which may contain a DNA template coding for a specific gene product, which specific gene product has
         A. an amino-terminal methioninyl residue, and
         B. an adjacent, second amino acid residue, both of which are also present as corresponding amino acid residues of one or more other gene products formed in the system, which second amino acid residue is incorporated in the system by a t-RNA isoacceptor species recognized by a codon for the second amino acid residue of the specific gene product but not by condons for the corresponding residues of the other gene products, with
      (ii) a mixture containing
         A. methioninyl t-RNA, and
         B. a second t-RNA which is the isoacceptor species recognized by the codon for the second amino acid residue of the specific gene product and which is charged with an amino acyl group corresponding to the second amino acid residue of the specific gene product, one or both of which t-RNA amino acyl groups is labeled, to allow formation of dipeptides;
   (b) incubating the reaction mixture for a period of time and at a temperature which would allow any dipeptide formation to be substantially complete;
   (c) adding a quantity of base that would be sufficient to stop any reaction and to hydrolyze any dipeptides formed from the t-RNA;
   (d) separating any dipeptides formed from the reaction mixture of step (c); and
   (e) detecting any separated dipeptides,
thereby detecting the synthesis of the specific gene product in the in vitro protein synthesizing system.

11. The method according to claim 10 in which a radiactive label is used.

12. The method according to claim 10 in which the in vitro protein synthesizing system comprises initiation factors, elongation factor Tu, ribosomes, buffers, salts, nucleoside triphosphates and RNA polyerase.

13. The method according to claim 12 in which the in vitro protein synthesizing system comprises Tris(hydroxymethyl)aminomethane-acetate, sodium dimethylglutarate, ammonium acetate, DTT, magnesium acetate, ATP, CTP, GTP, UTP, PEP, PK, potassium acetate, spermidine, PEG, RNA polymerase and NH4Cl-washed 70S ribosomes.

14. The method according to claim 10 in which any dipeptides formed are separated from the reaction mixture by thin layer chromatography or by ethyl acetate extraction.

15. The method according to claim 11 in which any separated dipeptides are detected by measuring the radioactivity of the radioactive label.

16. The method according to claim 10 in which the reaction mixture is incubated at about 37° C. for about 1 hour.

17. The method according to claim 10 in which the base is 1N NaOH.

18. The method according to claim 17 in which the base treatment is carried out at about 37° C. for about 10 minutes.

19. A method for detecting the synthesis of a specific gene product in an in vitro protein synthesizing system capable of carrying out transcription and translation, comprising:
   (a) reacting
      (i) an in vitro protein synthesizing system capable of carrying out transcription and translation which may contain a DNA template coding for a specific gene product, which specific gene product has
         A. an amino-terminal methioninyl residue and an adjacent, second amino acid residue, both of which are also present as correponding amino acid residues of one or more other gene products formed in the system, and
         B. a third amino acid residue adjacent to the second which differs from correspnding residues of all other gene products formed in the system, with
      (ii) a mixture containing
         A. methioninyl t-RNA, and
         B. second and third t-RNAs charged with amino acyl groups corresponding to the second and third amino acid residues of the specific gene product,
      one or more of which t-RNA amino acyl groups is labeled, to allow formation of tripeptides;
   (b) incubating the reaction mixture for a period of time and at a temperature which would allow any tripeptide formation to be substantially complete;
   (c) adding a quantity of base that would be sufficient to stop any reaction and to hydrolyze any tripeptides formed from the t-RNA;
   (d) separating any tripeptides formed from the reaction mixture of step (c); and
   (e) detecting any separated tripeptides, thereby detecting the synthesis of the specific gene product in the in vitro protein synthesizing system.

20. The method according to claim 19 in which a radioactive label is used.

21. The method according to claim 19 in which the in vitro protein synthesizing system comprises initiation factors, elongation factor Tu, ribosomes, buffers, salts, nucleoside triphosphates and RNA polymerase.

22. The method according to claim 21 in which the in vitro protein synthesizing system comprisees Tris(hydroxymethyl)aminomethane-acetate, sodium dimethylglutarate, ammonium acetate, DTT, magnesium acetate, ATP, CTP, GTP, UTP, PEP, PK, potassium acetate, spermidine, PEG, RNA polymerase and NH4Cl-washed 70S ribosomes.

23. The method according to claim 19 in which any tripeptides formed are separated from the reaction mixture by thin layer chromatography or by ethyl acetate extraction.

24. The method according to claim 20 in which any separated tripeptides are detected by measuring the radioactivity of the radiactive label.

25. The method according to claim 19 in which the reaction mixture is incubated at about 37° C. for about 1 hour.

26. The method according to claim 19 in which the base is 1N NaOH.

27. The method according to claim 26 in which the base treatment is carried out at about 37° C. for about 10 minutes.

* * * * *

UNITED STATES PATENT AND TRADEMARK OFFICE
CERTIFICATE OF CORRECTION

PATENT NO. : 4,661,443
DATED : April 28, 1987
INVENTOR(S) : Nathan Brot and Herbert Weissbach It is certified that error appears in the above-identified patent and that said Letters Patent are hereby corrected as shown below:

Column 12, line 51 Claim 4 "ATO" should be ATP

Column 13, line 20 Claim 10 "Condons" should be codons

Column 14, line 59 Claim 24 "radiactive" should be radioactive

Signed and Sealed this

Sixth Day of September, 1988

Attest:

DONALD J. QUIGG

*Attesting Officer*     *Commissioner of Patents and Trademarks*